(12) United States Patent
Tan

(10) Patent No.: US 12,036,263 B2
(45) Date of Patent: Jul. 16, 2024

(54) TOPICAL COMPOSITIONS

(71) Applicant: JYSK Skin Solutions PTE LTD, Singapore (SG)

(72) Inventor: Siak Khim Tan, Singapore (SG)

(73) Assignee: Illustris Pharmaceuticals, Inc., Irvine, CA (US)

( * ) Notice: Subject to any disclaimer, the term of this patent is extended or adjusted under 35 U.S.C. 154(b) by 0 days.

(21) Appl. No.: 17/869,665

(22) Filed: Jul. 20, 2022

(65) Prior Publication Data

US 2022/0354924 A1 Nov. 10, 2022

Related U.S. Application Data

(63) Continuation of application No. 16/920,460, filed on Jul. 3, 2020, now abandoned.

(60) Provisional application No. 62/870,154, filed on Jul. 3, 2019.

(51) Int. Cl.
| | |
|---|---|
| A61K 9/20 | (2006.01) |
| A61K 9/00 | (2006.01) |
| A61K 9/06 | (2006.01) |
| A61K 31/138 | (2006.01) |
| A61K 31/337 | (2006.01) |
| A61K 31/439 | (2006.01) |
| A61K 31/4545 | (2006.01) |
| A61K 31/4748 | (2006.01) |
| A61K 31/502 | (2006.01) |
| A61K 31/513 | (2006.01) |
| A61K 31/519 | (2006.01) |
| A61K 31/5377 | (2006.01) |
| A61K 31/675 | (2006.01) |
| A61K 31/704 | (2006.01) |
| A61K 31/7068 | (2006.01) |
| A61K 31/728 | (2006.01) |
| A61K 33/243 | (2019.01) |
| A61K 38/05 | (2006.01) |
| A61K 38/06 | (2006.01) |
| A61K 38/07 | (2006.01) |
| A61K 38/08 | (2019.01) |
| A61K 38/39 | (2006.01) |
| A61L 27/26 | (2006.01) |
| A61L 27/54 | (2006.01) |
| A61L 27/58 | (2006.01) |
| A61P 35/00 | (2006.01) |
| C12M 1/12 | (2006.01) |
| C12N 5/0775 | (2010.01) |
| C12N 5/09 | (2010.01) |
| G01N 33/50 | (2006.01) |

(52) U.S. Cl.
CPC ............ *A61K 38/08* (2013.01); *A61K 9/0014* (2013.01); *A61K 9/06* (2013.01); *A61K 31/728* (2013.01); *A61K 38/05* (2013.01); *A61K 38/06* (2013.01); *A61K 38/07* (2013.01); *A61K 38/39* (2013.01)

(58) Field of Classification Search
CPC ........ A61K 38/08; A61K 9/0014; A61K 9/06; A61K 31/728; A61K 38/05; A61K 38/06; A61K 38/07; A61K 38/39; A61K 8/64; A61K 8/65; A61K 8/735; A61Q 19/08
See application file for complete search history.

(56) References Cited

U.S. PATENT DOCUMENTS

| | | |
|---|---|---|
| 5,234,914 A | 8/1993 | Gallina |
| 5,646,129 A | 7/1997 | Callegaro et al. |
| 5,895,658 A | 4/1999 | Fossel |
| 6,271,216 B1 | 8/2001 | Mello et al. |
| 6,809,075 B1 | 10/2004 | Mitts et al. |
| 7,125,858 B2 | 10/2006 | Filion et al. |
| 7,495,076 B2 | 2/2009 | Gu et al. |
| 7,799,348 B2 | 9/2010 | Ishaq |
| 8,324,356 B2 | 12/2012 | Picotti et al. |
| 8,916,539 B2 | 12/2014 | Yedgar et al. |
| 9,012,395 B2 | 4/2015 | Calabro et al. |
| 9,050,336 B2 | 6/2015 | Blanda et al. |
| 9,149,534 B2 | 10/2015 | Leshshiner |
| 9,173,944 B2 | 11/2015 | Taylor et al. |
| 9,561,255 B2 | 2/2017 | Iwama et al. |
| 10,076,479 B1 | 9/2018 | Santhanam et al. |
| 2001/0022975 A1 | 9/2001 | Drizen et al. |
| 2001/0024658 A1 | 9/2001 | Chen et al. |
| 2004/0019010 A1 | 1/2004 | Karakelle et al. |
| 2004/0029970 A1 | 2/2004 | Rask-Andersen et al. |
| 2005/0048120 A1 | 3/2005 | Edgren et al. |
| 2005/0054578 A1 | 3/2005 | Sandberg et al. |
| 2005/0267068 A1 | 12/2005 | Back et al. |
| 2006/0177483 A1 | 8/2006 | Byrne et al. |

(Continued)

FOREIGN PATENT DOCUMENTS

| | | |
|---|---|---|
| BR | 112013016950 A2 | 4/2020 |
| CA | 1341087 C | 8/2000 |

(Continued)

OTHER PUBLICATIONS

Schagen et al. Cosmetics 2017, 4, 16. (Year: 2017).*

(Continued)

*Primary Examiner* — Erin E Hirt
*Assistant Examiner* — Janice Y Silverman
(74) *Attorney, Agent, or Firm* — McDermott Will & Emery LLP; Judy M. Mohr

(57) ABSTRACT

Compositions for dermal delivery of a topical solution and methods for using such compositions are described herein. The compositions may contain extracellular matrix components and therapeutic peptides.

21 Claims, No Drawings
Specification includes a Sequence Listing.

(56) References Cited

U.S. PATENT DOCUMENTS

| | | | |
|---|---|---|---|
| 2006/0182794 A1 | 8/2006 | Modi et al. |
| 2007/0020220 A1 | 1/2007 | Osborne |
| 2007/0077292 A1 | 4/2007 | Pinsky |
| 2007/0224150 A1 | 9/2007 | Chung |
| 2008/0045909 A1 | 2/2008 | Fossel |
| 2008/0050335 A1 | 2/2008 | Faour et al. |
| 2008/0220021 A1 | 9/2008 | Modi |
| 2009/0155314 A1 | 6/2009 | Tezel et al. |
| 2009/0220415 A1 | 9/2009 | Schachf et al. |
| 2009/0220497 A1 | 9/2009 | Brown et al. |
| 2010/0068232 A1 | 3/2010 | Key |
| 2010/0093686 A1 | 4/2010 | Chappa et al. |
| 2010/0112016 A1 | 5/2010 | Carli et al. |
| 2010/0124573 A1 | 5/2010 | Naughton et al. |
| 2010/0135935 A1 | 6/2010 | Leshchiner et al. |
| 2010/0160849 A1 | 6/2010 | Barbour |
| 2010/0172940 A1 | 7/2010 | Petrella |
| 2010/0210585 A1 | 8/2010 | Bresin et al. |
| 2010/0316724 A1 | 12/2010 | Whitfield et al. |
| 2010/0317588 A1 | 12/2010 | Shoseyov |
| 2011/0014241 A1 | 1/2011 | Cohen |
| 2011/0033402 A1 | 2/2011 | Modi |
| 2011/0033540 A1 | 2/2011 | Daniloff et al. |
| 2011/0189239 A1 | 8/2011 | Mansouri |
| 2011/0217249 A1 | 9/2011 | Drehar |
| 2011/0245335 A1 | 10/2011 | Prehm |
| 2012/0100194 A1 | 4/2012 | Yamai et al. |
| 2012/0141397 A1 | 6/2012 | Patel |
| 2012/0141532 A1 | 6/2012 | Blanda et al. |
| 2013/0045290 A1 | 2/2013 | Somerville |
| 2013/0059814 A1 | 3/2013 | Chaumont et al. |
| 2013/0078294 A1 | 3/2013 | Alexiades-Armenakas |
| 2013/0177505 A1 | 7/2013 | Somerville et al. |
| 2013/0236571 A1 | 9/2013 | Magdassi |
| 2014/0044797 A1 | 2/2014 | Johansson et al. |
| 2014/0072613 A1 | 3/2014 | Lander et al. |
| 2014/0228364 A1 | 8/2014 | Hadj-Slimane |
| 2014/0236082 A1 | 8/2014 | Roorda |
| 2014/0309157 A1 | 10/2014 | Chung et al. |
| 2015/0132237 A1 | 5/2015 | Leshchiner et al. |
| 2015/0157728 A1 | 6/2015 | Modi |
| 2015/0182554 A1 | 7/2015 | Koller et al. |
| 2015/0283045 A1 | 10/2015 | Hack et al. |
| 2015/0374633 A1 | 12/2015 | Fedorchak et al. |
| 2016/0000834 A1 | 1/2016 | Kinsey et al. |
| 2016/0053029 A1 | 2/2016 | Uha et al. |
| 2016/0089545 A1 | 3/2016 | Uuluri et al. |
| 2016/0199498 A1 | 7/2016 | Dai et al. |
| 2016/0324934 A1 | 11/2016 | Angel et al. |
| 2017/0100523 A1 | 4/2017 | Matheny |
| 2017/0189546 A1 | 7/2017 | Bidwell, III et al. |
| 2017/0202769 A1 | 7/2017 | Pilant |
| 2017/0216414 A1 | 8/2017 | Tezel et al. |
| 2017/0266267 A1 | 9/2017 | Osio |
| 2017/0290778 A1 | 10/2017 | Waugh |
| 2019/0008795 A1 | 1/2019 | Waugh |
| 2019/0105261 A1 | 4/2019 | Waugh |
| 2019/0254948 A1 | 8/2019 | Bader |
| 2020/0368150 A1 | 11/2020 | Damaj |
| 2021/0000910 A1 | 1/2021 | Tan |
| 2021/0093539 A1 | 4/2021 | LaRosa et al. |
| 2021/0137810 A1 | 5/2021 | Stasko et al. |
| 2021/0290737 A1 | 9/2021 | Cappello |
| 2021/0369596 A1 | 12/2021 | Carle et al. |

FOREIGN PATENT DOCUMENTS

| | | | | |
|---|---|---|---|---|
| CA | 2494473 A1 | 4/2005 | | |
| CA | 2761740 A1 | 11/2010 | | |
| CA | 2703532 A1 | 11/2011 | | |
| CH | 705713 B1 * | 5/2013 | ............ | A61K 8/735 |
| CH | 705713 B1 | 5/2013 | | |
| CH | 711092 A | 5/2015 | | |
| CN | 104721116 A | 6/2015 | | |
| CN | 105213298 A | 1/2016 | | |
| CN | 106726803 A * | 5/2017 | ............ | A61K 8/0212 |
| CN | 107913233 A * | 4/2018 | | |
| EP | 1262168 A1 * | 12/2002 | ............... | A61K 8/02 |
| EP | 2567689 A1 | 3/2013 | | |
| EP | 2922581 B1 | 3/2017 | | |
| FR | 2877574 A1 | 5/2006 | | |
| FR | 2971711 A1 | 8/2012 | | |
| JP | H07101831 A | 4/1995 | | |
| JP | 2001-139447 A | 5/2001 | | |
| WO | WO 2002/051380 A1 | 7/2002 | | |
| WO | WO 2007/021970 A2 | 2/2007 | | |
| WO | WO 2007/041627 A1 | 4/2007 | | |
| WO | WO 2008/003321 A2 | 1/2008 | | |
| WO | WO 2008/124169 A2 | 10/2008 | | |
| WO | WO 2010/009809 A2 | 1/2010 | | |
| WO | WO 2010/135527 A2 | 11/2010 | | |
| WO | WO 2014/044808 A2 | 3/2014 | | |
| WO | WO 2014/086679 A1 | 6/2014 | | |
| WO | WO 2014/134523 A1 | 9/2014 | | |
| WO | WO 2015/017601 A2 | 2/2015 | | |
| WO | WO 2016/112051 A1 | 7/2016 | | |
| WO | WO 2016/207340 A1 | 12/2016 | | |
| WO | WO 2017/180788 A1 | 10/2017 | | |

OTHER PUBLICATIONS

Albericio and Kruger, "Therapeutic peptides", Future Medicinal Chemistry, vol. 4, No. 12, pp. 1527-1531 (2012).

Bentov et al. "The effect of aging on the cutaneous microvasculature", Microvasc. Res., vol. 100, pp. 25-31 (2015).

Bruch-Gerharz et al., "Nitric oxide in human skin: current status and future prospects", J. Invest. Dermatol., vol. 110, No. 1, pp. 1-7 (1998).

Czech et al., "Collagen Peptides—Source, Properties, and Benefits", Seagarden AS, Online article downlaoded from www.seagarden.no, 7 pages (2016).

Essendoubi et al., "Human skin penetration of hyaluronic acid of different molecular weights as probed by Raman spectroscopy", Skin Res. Tech., pp. 1-8 (2015).

Gad, "Anti-aging effects of l-arginine", J. Adv. Res., vol. 1, Issue 3, pp. 169-177 (2010).

Gura, "Systems for identifying new drugs are often faulty", Science, vol. 278, No. 5340, pp. 1041-1042 (1997).

Habibi et al., "Self-assembled peptide-based nanostructures: Smart nanomaterials toward targeted drug delivery", Nano Today, vol. 11, No. 1, pp. 41-60 (2016).

International Search Report and Written Opinion from International Application No. PCT/US2017/27275, 8 pages, dated Jul. 14, 2017.

International Search Report and Written Opinion from International Application No. PCT/US2018/055499, 9 pages, dated Dec. 27, 2018.

Kim et al. "Age-related changes in skin bio-mechanical properties: the neck skin compared with the cheek and forearm skin in Korean females", Skin Res. Technol., vol. 19, No. 3, pp. 236-241 (2013).

Laver et al., "Regulation of the calcium release channel from rabbit skeletal muscle by the nucleotides ATP, AMP, IMP and adenosine", J. Phys., vol. 537, No. 3, pp. 763-778 (2001).

Laver, "Coupled calcium release channels and their regulation by luminal and cytosolic ions", Eur. Biophys. J., vol. 34, pp. 359-368 (2005).

Martins et al., "Design of Novel BSA/Hyaluronic Acid Nanodispersions for Transdermal Pharma Purposes," Molecular Pharmaceutics, vol. 11, pp. 1479-1488 (2014).

Mirza and Khatri, "", The use of lasers in the treatment of skin cancer: A review, J. Cosmetic and Laser Therapy, vol. 19, No. 8, pp. 451-458 (2017).

Murayama et al., "Role of Mg21 in Ca21-Induced Ca21 Release through Ryanodine Receptors of Frog Skeletal Muscle: Modulations by Adenine Nucleotides and Caffeine", Biophysical J., vol. 78, pp. 1810-1824 (2000).

Ryan et al., "The ageing of the blood supply and the lymphatic drainage of the skin", Micron., vol. 35, No. 3, pp. 161-171 (2004).

(56) References Cited

OTHER PUBLICATIONS

Samy et al., "Novel microstructured sildenafil dosage forms as wound healing promoters", Expert Opinion on Drug Delivery, vol. 11, No. 10, pp. 1525-1536 (2014).
Shrewsbury, Applied Pharmaceutics in Contemporary Compounding, Chapter 17, pp. 229-230 (2015).
Takahashi et al., "Carnosine Facilitates Nitric Oxide Production in Endothelial F-2 Cells", Biol. Pharm. Bull., vol. 31, No. 11, pp. 1836-1839 (2009).
Techno™ Neck Perfecting Cream, *Promotional Brochure*, Skinbetter Science, Phoenix, AZ 85018, 16 pages (2021).
Tripodo et al., "Hyaluronic acid and its derivatives in drug delivery and imaging: Recent advances and challenges", European J. Pharm. Biopharm., vol. 97, pp. 400-416 (2015).
Xie et al., "Hyaluronic Acid: Evaluation as a Potential Delivery Vehicle for Vitronectin: Growth Factor Complexes in Would Healing Applications" *Authors version submitted/accepted for publication in*, Journal of Controlled Release, vol. 153 pp. 225-232 (2011), Downloaded from: http://eprints.qut.edu.au/46400/.
Yang et al., "Transdermal delivery of hyaluronic acid—Human growth hormone conjugate" Biomaterials, vol. 33, pp. 5947-5954 (2012).
Zhang et al., "Cosmetics and peptides", Clinics in Dermatology, vol. 27, pp. 485-494 (2009).

\* cited by examiner

TOPICAL COMPOSITIONS

CROSS-REFERENCE TO RELATED APPLICATIONS

This application is a continuation of U.S. application Ser. No. 16/920,460, filed Jul. 3, 2020, which claims the benefit of priority to U.S. Provisional Patent Application No. 62/870,154, filed Jul. 3, 2019, each of which is incorporated herein by reference in its entirety.

SEQUENCE LISTING

The instant application contains a substitute Sequence Listing which has been filed electronically in XML format and is hereby incorporated by reference in its entirety. Said XML copy, created on Jul. 6, 2023, is named 090471-0025-8003US01 SUBSEQ Listing.xml and is 8,930 bytes in size.

BRIEF SUMMARY

Various embodiments are directed to compositions including an extracellular matrix component or fragment thereof having a concentration of about 0.1 wt. % to about 5 wt. % based on the total weight composition and a therapeutic peptide having a concentration of about 0.1 wt. % to about 25 wt. % based on the total weight composition. In some embodiments, the extracellular matrix component or fragment thereof may be hyaluronic acid, collagen, fibronectin, elastin, lectin, and the like and combinations thereof, and in some embodiments, collagen may be collagen type I, collagen type II, collagen type III, collagen type IV, collagen type V, fibrillary collagen, non-fibrillary collagen, and combinations thereof. In some embodiments, the therapeutic peptide may be palmitoyl oligopeptide, palmitoyl tripeptide-1, palmitoyl tetrapeptide-7, acetyl hexapeptide-3, and the like and combinations thereof. In some embodiments, the composition may include about 1 mg to about 1000 mg of the extracellular matrix component or a fragment thereof, and in some embodiments, the composition may include about 1 mg to about 1000 mg therapeutic peptide. In some embodiments, the concentration of therapeutic peptide may be about 5 wt. % to 20 wt. %, and in some embodiments, the therapeutic peptide may be dipeptides, tripeptides, tetrapeptides, pentapeptides, hexapeptides, dipeptide derivatives, tripeptides derivatives, tetrapeptides derivatives, pentapeptides derivatives, hexapeptides derivatives, and the like and combinations thereof.

The composition may include one or more pharmaceutical additives such as, for example, diluents, fillers, disintegrants, binders, lubricants, surfactants, hydrophobic vehicles, water soluble vehicles, emulsifiers, buffers, humectants, moisturizers, solubilizers, preservatives, colorants, plasticizers, carriers, excipients, or combinations thereof, and in some embodiments, the composition may include one or more cosmetic additives such as vitamins, cosmetic peptides, oil control agents, other skin care agents, and hydrating compositions. Such composition may be formulated as a liquid, cream, ointment, gel, or the like.

Additional embodiments are directed to methods for treating skin by topically administering the compositions described above.

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey the scope to those skilled in the art.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 mare also explicitly disclosed, as well as the range of values greater than or equal to 1 µm and the range of values less than or equal to 8 µm.

The singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

The compositions of the present disclosure can comprise, consist essentially of, or consist of, the components disclosed.

All percentages, parts and ratios are based upon the total weight of the topical compositions and all measurements made are at about 25° C., unless otherwise specified.

The word "about" when immediately preceding a numerical value means a range of plus or minus 10% of that value, e.g., "about 50" means 45 to 55, "about 25,000" means 22,500 to 27,500, etc, unless the context of the disclosure indicates otherwise, or is inconsistent with such an interpretation. For example, in a list of numerical values such as "about 49, about 50, about 55, "about 50" means a range extending to less than half the interval(s) between the preceding and subsequent values, e.g, more than 49.5 to less than 52.5. Furthermore, the phrases "less than about" a value or "greater than about" a value should be understood in view of the definition of the term "about" provided herein.

The terms "administer," "administering" or "administration" as used herein refer to directly administering a compound (also referred to as an agent of interest).

As used herein, the term "cosmetic" or "cosmetics" are substances or products used to enhance or alter the appearance of the face or body often called "make-up" or "makeup." The terms "skin care composition" or "skin care product" is used to describe compositions that clean or treat skin, and include, for example, cleansers, lotions, soaps, balms, foams, and the like.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical, cosmetic or other agent across a tissue layer such as the stratum corneum or stratum spinosum.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The phrase "pharmaceutically acceptable" is employed herein to refer to those agents of interest/compounds, salts, compositions, dosage forms, etc, which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, "pharmaceutically acceptable" means approved by a regulatory agency of the federal or a state government, or listed in the U.S. Pharmacopeia or other generally recognized pharmacopeia for use in mammals (e.g, animals), and more particularly, in humans.

The term "salts" as used herein embraces pharmaceutically acceptable salts commonly used to form alkali metal salts of free acids and to form addition salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid.

The term "patient," "subject," and "user" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

The term "treating" is used herein, for instance, in reference to methods of treating a skin disorder or a systemic condition, and generally includes the administration of a compound or composition which reduces the frequency of, or delays the onset of, symptoms of a medical condition in a subject relative to a subject not receiving the compound or composition. This can include reversing, reducing, or arresting the symptoms, clinical signs, and underlying pathology of a condition in a manner to improve or stabilize a subject's condition.

By reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason. Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Various embodiments of the invention are directed to topical compositions containing a combination of an extracellular matrix molecule and a therapeutic peptide, and methods for treating disorders of the epidermis or skin using such topical compositions. The compositions of embodiments may create an optimal environment for the body's innate processes of repair and renewal and ensure absorption and delivery of essential ingredients.

"Topical administration" is used in its conventional sense to mean delivery of a composition to the skin or mucosa, as in, for example, the treatment of various skin disorders. Topical administration, in contrast to transdermal administration, provides a local rather than a systemic effect. However, unless otherwise stated or implied, the terms "topical product administration" and "transdermal product administration" are used interchangeably.

In certain embodiments, the extracellular matrix molecule may be a fragment of an extracellular matrix component or a receptor associated with the extracellular matrix. For example, in some embodiments, the extracellular matrix molecule may be hyaluronic acid, elastin, collagen, fibronectin, lectin, and the like and combinations thereof.

In various embodiments, the extracellular matrix molecule may have an average molecular weight of less than 100,000 Daltons ("Da"). In particular embodiments, the extracellular matrix molecule may have an average molecular weight of about 2,000 Da to about 60,000, about 2,000 Da to about 40,000 Da, or about 5,000 Da to about 40,000 Da.

In general, the amount of extracellular matrix molecules present in the compositions of various embodiments may be from about 0.1 wt. % to about 10 wt. %, and in particular embodiments, the amount of extracellular matrix molecules in such compositions may be from about 0.1 wt. % to about 2.0 wt. %, about 0.25 wt. % to about 3.0 wt. %, about 0.5 wt. % to about 5.0 wt. %, about 0.75 wt. % to about 7.5 wt. %, or any range or individual concentration encompassing these example ranges. In some embodiments, the amount of extracellular matrix molecules in a composition may be about 1 mg to about 1000 mg, about 1 mg to about 900 mg, about 1 mg to about 800 mg, about 1 mg to about 700 mg, about 1 mg to about 600 mg, about 1 mg to about 500 mg, about 1 mg to about 400 mg, about 1 mg to about 300 mg, about 1 mg to about 200 mg, about 1 mg to about 100 mg, about 10 mg to about 1000 mg, about 50 mg to about 1000 mg, about 100 mg to about 1000 mg, about 200 mg to about 1000 mg, about 300 mg to about 1000 mg, about 400 mg to about 1000 mg, about 500 mg to about 1000 mg, about 10 mg to about 500 mg, about 50 mg to about 500 mg, about 100 mg to about 500 mg, about 10 mg to about 300 mg, about 50 mg to about 300 mg, from about 100 mg to about 300 mg, about 10 mg to about 150 mg, about 50 mg to about 150 mg, about 60 mg to about 120 mg, about 50 mg to about 120 mg or a range between any two of these values.

In particular embodiments, the extracellular matrix molecule may be hyaluronic acid. Hyaluronic acid is known to interact with, for example, CD44, receptor for hyaluronic acid-mediated motility (RHAMM), and intercellular adhesion molecule-I (ICAM-1). CD44 is widely distributed throughout the body and mediates cell interaction with hyaluronic acid. ICAM-1 is a metabolic cell surface receptor for hyaluronic acid, and binding of hyaluronic acid to ICAM-1 may contribute to the control of ICAM-1-mediated inflammatory activation. Hyaluronic acid is polymer of disaccharides. Without wishing to be bound by theory, low molecular weight fragments of hyaluronic acid may disrupt cell-cell and cell-scaffold attachments by interrupting intercellular interactions and/or by triggering cellular injury response, which may disrupt intercellular interactions between cells that do not directly contact the hyaluronic acid molecule.

In some embodiments, the extracellular matrix molecule may be collagen. Collagen can be isolated in various forms and from a number of sources. Example collagens include collagen type I, collagen type II, collagen type III, collagen type IV, or collagen type V. The collagen can also be fibrillary collagen or non-fibrillar collagen. Low molecular weight collagens can be made, for example, by hydrolysis, and like hyaluronic acid, low molecular weight collagen may disrupt cell-cell and cell-scaffold attachments by interrupting intercellular interactions and/or by triggering cellular injury response, which may disrupt intercellular interactions between cells deeper in the tissue.

In certain embodiments, the extracellular matrix molecule may be fibronectin. Fibronectin is a protein dimer, consisting of two nearly identical monomers linked by a pair of disulfide bonds. Fibronectin binds to membrane-spanning receptor proteins called integrins and extracellular matrix components such as collagen, fibrin, and heparin sulfate proteoglycans. Like hyaluronic acid and collagen, fibronectin fragments may disrupt cell-cell and cell-scaffold attachments by interrupting intercellular interactions and/or by triggering cellular injury response, which may disrupt intercellular interactions between cells deeper in the tissue.

In some embodiments, the extracellular matrix molecule may be elastin. Elastin is a protein found in connective tissue and allows many tissues in the body to resume their shape after stretching or contracting. Like hyaluronic acid, collagen, and fibronectin, elastin fragments may disrupt cell-cell and cell-scaffold attachments by interrupting intercellular interactions and/or by triggering cellular injury response, which may disrupt intercellular interactions between cells deeper in the tissue.

The therapeutic peptides of various embodiments include, without limitation, the di-, tri-, terra-, penta- and hexapeptides and their derivatives. The term "peptide" refers to peptides containing 10 amino acids or less, their derivatives, isomers and complexes with other species such as a metallic ion (e.g. copper, zinc, manganese, magnesium, and others). The term "peptides" refers to both natural peptides and synthetic peptides. It also refers to compositions that contain peptides that are found in nature, isolated from natural sources, synthesized, are commercially available, and the like.

Dipeptides encompassed by the invention include, but are not limited to, carnosine (beta-AH), YR, VW, NF, DF, KT, KC, CK, KP, KK, TT, and the like and combinations thereof. Tripeptides include, but are not limited to, RKR, HGG, GKH, GGH, GHG, KFK, KPK, KMOK, KM02K, KAvaK, and the like and combinations thereof. Tetrapeptides include, but are not limited to, RSRK, KTFK, and the like and combinations thereof. Non-limiting examples of pentapeptide include KTTKS (SEQ ID NO: 1) and the like and of hexapeptides the GKTTKS (SEQ ID NO: 2), VGVAPG (SEQ ID NO: 3), and the like and combinations thereof.

Other suitable therapeutic peptides include, but are not limited to, lipophilic derivatives of peptides, including, for example, palmitoyl derivatives and metal complexes such as, for example, a copper complex of the tripeptide HGG. Dipeptide derivatives include Pal-beta-AH, Ac-YR-hexadecylester, Pal-KT, Pal-RT, and the like and combinations thereof. Tripeptide derivatives include the copper derivative of HGG, Lipospondin (Ela-KFK) and its analogs, Ac-RKR-NH2 (Peptide CK+), Pal-KM02K, and the like and combinations thereof. Tetrapeptide derivatives include Ela-KTFK, and pentapeptide derivatives include, Pal-KTTKS (SEQ ID NO: 4), Pal-YGGFX (SEQ ID NO: 5) with X being Met(M) or Leu(L) and the like and combinations thereof. Hexapeptide derivatives include Pal-VGVAPG (SEQ ID NO: 6), Pal-GKTTKS (SEQ ID NO: 7), and the like and combinations and derivatives thereof. In certain embodiments, the compositions may include a combination of various dipeptides, tripeptides, tetrapeptides, pentapeptides, hexapeptides, dipeptide derivatives, tripeptides derivatives, tetrapeptides derivatives, pentapeptides derivatives, hexapeptides derivatives, and the like.

The following commercially available therapeutic peptides can be mentioned as well as additional active ingredients: Vialox™, Syn-ake™ or Syn-Coll™ (Pentapharm), Hydroxyprolisilane CN™ (Exsymol), Argireline™, Leuphasyl™, Aldenine™, Trylgen™, Eyeseryl™, Serilesine™ or Decorinyl™ (Lipotec), Collaxyl™ or Quintescine™ (Vincience), BONT-L-Peptide™ (Infinitec Activos), Cytokinol™LS (Laboratoires Serobiologiques/Cognis), Kollaren™, IP2000™ or Meliprene™ (Institut Europeen de Biologie Cellulaire), Neutrazen™ (Innovations), ECM-Protect™ (Atrium Innovations), Timp-Peptide™, ECM Moduline™ (Infinitec Activos). Palmitoyl oligopeptide (e.g., palmitoyltripeptide) and/or palmitoyltetrapeptide-7, and derivatives thereof, commonly known as MATRIXYL™3000 (manufactured by Sederma, SA), is a blend of two or more peptide complexes. Palmitoyloligopeptide (e.g., palmitoyltripeptide), as set forth above, is a peptide comprised of 3 amino acids: Glycine Histidine-Lysine (N-palmitoyl-Gly-His-Lys). In some embodiments, therapeutic peptides may include palmitoyl tetrapeptide-7. This therapeutic peptide may be composed of four amino acids plus fatty acid palmitic acid to enhance stability and penetration into the skin. Therapeutic peptides have different functions on skin, and this particular peptide, on its own or as part of Matrixyl 3000, helps to replenish the skin's surface and calm visible signs of sensitization.

In some embodiments, therapeutic peptides may include acetyl hexapeptide-3, otherwise known as argireline. This therapeutic peptide may bind to the SNARE-receptor, blocking the production of neurotransmitter which then reduces facial muscle contraction. It has been used as a replacement for BOTOX®. Formulations with 10% concentration acetyl hexapeptide have been shown to reduce the depth of wrinkles up to 30% after 30 days of trial use. The skincare composition may include hexapeptide complexes having hexapeptide concentrations ranging from approximately 0.00001 to approximately 15% w/w, preferably from 0.01% w/w to 10% w/w, and more preferably from 0.1 to 5%.

Particular examples of compositions encompassed by the invention include compositions containing about 0.1 wt. % to about 2.0 wt. % extracellular matrix molecule having an average molecular weight of about 2,000 Da to about 60,000

Da, and a peptide such as palmitoyl oligopeptide (palmitoyl tripeptide-1, palmitoyl tetrapeptide-7, acetyl hexapeptide-3, and peptides of similar size and combinations thereof.

In some embodiments, the compositions described above may further include one or more pharmaceutically acceptable diluents, fillers, disintegrants, binders, lubricants, surfactants, hydrophobic vehicles, water soluble vehicles, emulsifiers, buffers, humectants, moisturizers, solubilizers, preservatives, colorants, plasticizers, carriers, excipients, and the like and combinations thereof. The person of ordinary skill in the art can refer to various pharmacologic references such as, for example, Modern Pharmaceutics, Banker & Rhodes, Marcel Dekker, Inc. (1979) and Goodman & Gilman's The Pharmaceutical Basis of Therapeutics, 6th Edition, MacMillan Publishing Co, New York (1980) for guidance in determining the amount of such components in the compositions and formulations of embodiments.

In some embodiments, the compositions described above may be formulated as a liquid. Liquid dosage forms for topical administration may include diluents such as, for example, alcohols, glycols, oils, water, and the like. Such compositions may also include wetting agents or emulsifiers. In some embodiments, the compositions of embodiments may be formulated as oil-in-water or water-in-oil emulsion. A cream can be a water-in-oil (w/o) emulsion in which an aqueous phase is dispersed in an oil phase, or an oil-in-water (o/w) emulsion in which an oil is dispersed within an aqueous base. An ointment generally refers to a more viscous oil-in-water cream. Traditional ointment bases (i.e. carrier) include hydrocarbons (petrolatum, beeswax, etc.) vegetable oils, fatty alcohols (cholesterol, lanolin, wool alcohol, stearyl alcohol, etc.) or silicone. Insoluble solids such as starch, zinc oxide, calcium carbonate, or talc can also be used in ointments and creams. Gel forms of the compositions described above can be formed by the entrapment of large amounts of aqueous or aqueous-alcoholic liquids in a network of polymers or of colloidal solid particles. Such polymers or colloids (gelling or thickening agents) are typically present at concentrations of less than 10% w/w and include carboxymethyl cellulose, hydroxypropylmethyl cellulose, hydroxyethyl cellulose, methyl cellulose, sodium alginate, alginic acid, pectin, tragacanth, carrageen, agar, clays, aluminum silicate, carbomers, and the like.

Emollient or lubricating vehicles that help hydrate the skin can also be used. Examples of suitable bases or vehicles for preparing hydrating compositions for use with human skin are petrolatum, petrolatum plus volatile silicones, lanolin, cold cream (USP), and hydrophilic ointment (USP).

In certain embodiments, the compositions of various embodiments may be formulated for improving appearance of skin and may additionally include additives such as vitamins, cosmetic peptides, oil control agents, and other skin care agents.

Vitamins include, for example, vitamin D, vitamin K, vitamin B (including niacinamide, nicotinic acid, $C_{1-18}$ nicotinic acid esters, and nicotinyl alcohol; B6 compounds, such as pyridoxine; and B5 compounds, such as panthenol, or "pro-B5"), vitamin A (including retinoids such as retinyl propionate, carotenoids, and other compounds), vitamin E (including tocopherol sorbate, tocopherol acetate, other esters of tocopherol), vitamin C (including ascorbyl esters of fatty acids, and ascorbic acid derivatives, for example, ascorbyl glucoside, magnesium ascorbyl phosphate, sodium ascorbyl phosphate, and ascorbyl sorbate), and all natural and/or synthetic analogs thereof, and combinations thereof. In various embodiments, the compositions may include about 0.0001 wt. % to about 50 wt. %, about 0.001 wt. % to about 10 wt. %, about 0.01 wt. % to about 5 wt. %, or about 0.1 wt. % to about 1 wt. %, or any individual concentration or range of each vitamin contained in the composition.

Peptides include di-, tri-, tetra-, penta-, and hexa-peptides, their salts, isomers, derivatives, and mixtures thereof. Examples of useful peptide derivatives include, but are not limited to, peptides derived from soy proteins, palmitoyl-lysine-threonine (pal-KT) and palmitoyl-lysine-threonine-threonine-lysine-serine (MATRIXYL®) palmitoyl-glycine-glutamine-proline-arginine (RIGIN®), these three being available from Sederma, France, and Cu-histidine-glycine-glycine (Cu-HGG, also known as TAMING), and naturally occurring and synthesized derivatives thereof, and combinations thereof. In various embodiments, the compositions may include about 1×10-7 wt. % to about 20 wt. %, about 1×10-6 wt. % to about 10 wt. %, and about 1×10-5 wt. % to about 5 wt. %, or any individual concentration or range of each peptide contained in the composition.

Oil control agents include compounds useful for regulating the production of skin oil, or sebum, and for improving the appearance of oily skin. Examples of oil control agents include, for example, salicylic acid, dehydroacetic acid, benzoyl peroxide, vitamin B3 (for example, niacinamide), and the like, their isomers, esters, salts and derivatives, and mixtures thereof. The compositions of such embodiments may include about 0.0001 wt. % to about 15 wt. %, about 0.01 wt. % to about 10 wt. %, about 0.1 wt. % to about 5 wt. %, and about 0.2 wt. % to about 2 wt. %, or any individual concentration or range of each oil control agent contained in the composition.

Other skin care agents include retinal, steroids, sunblock, salicylate, minocycline, antifungals, peptides, antibodies, lidocaine, and the like and combinations thereof. In some embodiments, other skin care agents include N-acyl amino acid compounds including, for example, N-acyl phenylalanine, N-acyl tyrosine, and the like, their isomers, including their D and L isomers, salts, derivatives, and mixtures thereof. An example of a suitable N-acyl amino acid is N-undecylenoyl-L-phenylalanine is commercially available under the tradename SEPIWHITE®. Further skin care agents are disclosed in U.S. Publication No. 2007/0020220A1, wherein the components/ingredients are incorporated herein by reference in their entirety.

Some embodiments may include the step of administering the composition to a surface tissue. For example, such methods may include the step of applying a composition or formulation such as those described above including an extracellular matrix molecule and a peptide to a surface tissue of a subject.

As indicated above, a "surface tissue" includes any surface tissue such as, but not limited to, skin surfaces of the face, hands, neck, and the like. The methods of such embodiments may include a variety of additional steps including, for example, cleaning the surface tissue at the site of applying and the like. In such embodiments, the composition can be applied to the surface tissue one or more times each day, and applying can be carried out for a period of at least 1 month, 2 months, 3 months, 4 months, 6 months, 8 months or 12 months.

The methods of embodiments may be used for administration of various cosmetic therapies for improving, for example, skin thickness, elasticity, resiliency, smoothness, tone, texture, brightness, clarity, contour, firmness, tautness, suppleness, discoloration, skin lesions, and the like and combinations thereof.

SEQUENCE LISTING

```
Sequence total quantity: 7
SEQ ID NO: 1            moltype = AA  length = 5
FEATURE                 Location/Qualifiers
source                  1..5
                        mol_type = protein
                        organism = synthetic construct
SEQUENCE: 1
KTTKS                                                                       5

SEQ ID NO: 2            moltype = AA  length = 6
FEATURE                 Location/Qualifiers
source                  1..6
                        mol_type = protein
                        organism = synthetic construct
SEQUENCE: 2
GKTTKS                                                                      6

SEQ ID NO: 3            moltype = AA  length = 6
FEATURE                 Location/Qualifiers
source                  1..6
                        mol_type = protein
                        organism = synthetic construct
SEQUENCE: 3
VGVAPG                                                                      6

SEQ ID NO: 4            moltype = AA  length = 5
FEATURE                 Location/Qualifiers
source                  1..5
                        mol_type = protein
                        organism = synthetic construct
MOD_RES                 1
                        note = modified with palmitoyl
SEQUENCE: 4
KTTKS                                                                       5

SEQ ID NO: 5            moltype = AA  length = 5
FEATURE                 Location/Qualifiers
source                  1..5
                        mol_type = protein
                        organism = synthetic construct
MOD_RES                 1
                        note = modified with palmitoyl
VARIANT                 5
                        note = X is M or L
SEQUENCE: 5
YGGFX                                                                       5

SEQ ID NO: 6            moltype = AA  length = 6
FEATURE                 Location/Qualifiers
source                  1..6
                        mol_type = protein
                        organism = synthetic construct
MOD_RES                 1
                        note = modified with palmitoyl
SEQUENCE: 6
VGVAPG                                                                      6

SEQ ID NO: 7            moltype = AA  length = 6
FEATURE                 Location/Qualifiers
source                  1..6
                        mol_type = protein
                        organism = synthetic construct
MOD_RES                 1
                        note = modified with palmitoyl
SEQUENCE: 7
GKTTKS                                                                      6
```

The invention claimed is:

1. A composition, comprising:
an extracellular matrix component and a therapeutic peptide,
wherein the extracellular matrix component consists of an extracellular matrix component with an average molecular weight of less than about 100,000 Daltons, wherein the extracellular matrix component is at a concentration of about 0.1 wt. % to about 5 wt. % based on the total weight of the composition; and
wherein the therapeutic peptide is at a concentration of about 5 wt. % to about 25 wt. % based on the total weight of the composition.

2. The composition of claim 1, wherein the extracellular matrix component or fragment thereof is selected from the group consisting of hyaluronic acid, collagen, fibronectin, elastin, lectin, and a combination thereof.

3. The composition of claim 2, wherein collagen is selected from the group consisting of collagen type I, collagen type II, collagen type III, collagen type IV, collagen type V, fibrillary collagen, non-fibrillary collagen, and a combination thereof.

4. The composition of claim 1, wherein the therapeutic peptide is selected from the group consisting of palmitoyl oligopeptide, palmitoyl tripeptide-1, palmitoyl tetrapeptide-7, acetyl hexapeptide-3, and combinations thereof.

5. The composition of claim 1, comprising about 1 mg to about 1000 mg of the extracellular matrix component or a fragment thereof.

6. The composition of claim 1, comprising about 1 mg to about 1000 mg therapeutic peptide.

7. The composition of claim 1, wherein the concentration of therapeutic peptide is about 5 wt. % to 20 wt. %.

8. The composition of claim 1, further comprising one or more pharmaceutical additives selected from the group consisting of diluents, fillers, disintegrants, binders, lubricants, surfactants, hydrophobic vehicles, water soluble vehicles, emulsifiers, buffers, humectants, moisturizers, solubilizers, preservatives, colorants, plasticizers, carriers, excipients, and a combination thereof.

9. The composition of claim 1, wherein the therapeutic peptide is selected from the group consisting of dipeptides, tripeptides, tetrapeptides, pentapeptides, hexapeptides and a combination thereof.

10. The composition of claim 1, wherein the composition is formulated as a liquid, cream, ointment, or gel.

11. A method for enhancing or altering appearance of skin, comprising: topically administering a composition comprising an extracellular matrix component and a therapeutic peptide,
   wherein the extracellular matrix component consists of an extracellular matrix component with an average molecular weight of less than about 100,000 Daltons, wherein the extracellular matrix component is at a concentration of about 0.1 wt. % to about 5.0 wt. % based on the total weight of the composition, and wherein the therapeutic peptide is at a concentration of about 5 wt. % to about 25 wt. % based on the total weight of the composition.

12. The method of claim 11, wherein the extracellular matrix component or fragment thereof is selected from the group consisting of hyaluronic acid, collagen, fibronectin, elastin, lectin, and fragments and combinations thereof.

13. The method of claim 11, wherein the composition comprises about 1 mg to about 1000 mg of the extracellular matrix component or a fragment thereof.

14. The method of claim 13, comprising about 0.1 wt. % to about 25 wt. % of other components.

15. The composition of claim 9, wherein the therapeutic peptide is a palmitoyl oligopeptide.

16. The composition of claim 15, wherein the therapeutic peptide is selected from the group consisting of palmitoyl tripeptide-1, palmitoyl tetrapeptide-7, palmitoyl-lysine-threonine, palmitoyl-lysine-threonine-threonine-lysine-serine, N-palmitoyl-glycine-histidine-lysine, palmitoyl-glycine-glutamine-proline-arginine, palmitoyl-VGVAPG, palmitoyl-GKTTKS, and palmitoyl-YGGFX, where X is Met(M) or Leu(L).

17. The composition of claim 9, wherein the therapeutic peptide is selected from the group consisting of acetyl hexapeptide-3 and Cu-histidine-glycine-glycine.

18. The composition of claim 1, further comprising a vitamin selected from the group consisting of vitamin D, vitamin K, vitamin B, vitamin A, vitamin E, and vitamin C, or a combination thereof.

19. The composition of claim 1, further comprising an oil control agent selected from the group consisting of salicylic acid, dehydroacetic acid, benzoyl peroxide, and vitamin B3, or a mixture thereof.

20. The composition of claim 1, further comprising a skin care agent selected from the group consisting of retinal, salicylate, minocycline, and lidocaine.

21. The composition of claim 1, further comprising a hydrating composition, which is a lubricating vehicle, which is selected from the group consisting of petrolatum, petrolatum plus volatile silicone, lanolin, cold cream, and hydrophilic ointment.

* * * * *